United States Patent [19]

Ramirez

[11] Patent Number: 5,735,598
[45] Date of Patent: Apr. 7, 1998

[54] SURGICAL LIGHT HANDLE COVER

[75] Inventor: Bruno J. Ramirez, Simi Valley, Calif.

[73] Assignee: Graphic Controls Corporation, Buffalo, N.Y.

[21] Appl. No.: 603,011

[22] Filed: Feb. 16, 1996

Related U.S. Application Data

[63] Continuation of Ser. No. 491,394, Jun. 19, 1995, abandoned.

[51] Int. Cl.⁶ ............................................. F21L 15/12
[52] U.S. Cl. ..................... 362/400; 362/804; 16/114 R; 206/438
[58] Field of Search ........................... 362/399, 400, 362/804; 16/114 A, 114 R, DIG. 24; 206/223, 438, 439, 570

[56] References Cited

U.S. PATENT DOCUMENTS

| D. 289,206 | 4/1987 | Scoville, Jr. et al. | D26/140 |
|---|---|---|---|
| D. 313,670 | 1/1991 | Barron et al. | D26/113 |
| 4,316,237 | 2/1982 | Yamada et al. | 362/33 |
| 4,559,671 | 12/1985 | Andrews et al. | 16/111 R |
| 4,605,124 | 8/1986 | Sandel et al. | 206/223 |
| 4,739,883 | 4/1988 | Mohs et al. | 206/470 |
| 4,844,252 | 7/1989 | Barron et al. | 206/223 |
| 4,878,156 | 10/1989 | Hallings et al. | 362/109 |
| 4,974,288 | 12/1990 | Reasner | 16/114 R |
| 4,976,299 | 12/1990 | Bickelman | 362/804 X |
| 5,036,446 | 7/1991 | Quintanilla et al. | 362/399 |
| 5,065,296 | 11/1991 | Cude | 362/399 |
| 5,156,267 | 10/1992 | Yates, Jr. et al. | 206/364 |
| 5,273,157 | 12/1993 | Spina | 362/804 X |
| 5,355,292 | 10/1994 | Hoftman et al. | 362/400 |
| 5,493,757 | 2/1996 | Horan et al. | 16/114 R |
| 5,604,955 | 2/1997 | Horan | 16/114 R |

OTHER PUBLICATIONS

Brochure, "Another New Product From Devon, EZ Handle", 1992, CA–3641–1, 100592, Devon Industries, Inc. (1 pg.).
Brochure, "Devon Lite Handle System EZ Handle", 1994, CA–3640, 150394, Devon Industries, Inc. (1 pg.).

*Primary Examiner*—Stephen F. Husar
*Attorney, Agent, or Firm*—Lyon & Lyon LLP

[57] ABSTRACT

A removable handle for a surgical light fixture includes a tubular handle, a circular shield, and a threaded portion. The circular shield includes two living hinges which permit the shield to be folded down against the handle for storage. A plurality of tabs are disposed on the lower face of the shield, and a matching indentation is formed on the lower end of the handle, to enable two handles to be frictionally engaged together by engaging the tabs of one handle with the indentations of the other. The handle is attached to a light fixture by means of an adapter which includes at least one projecting portion which presses against and deforms the circular shield and prevent the living hinges from hinging, thereby causing the folding portions of the circular shield to be held rigidly in place while the handle is attached to the light fixture.

9 Claims, 4 Drawing Sheets

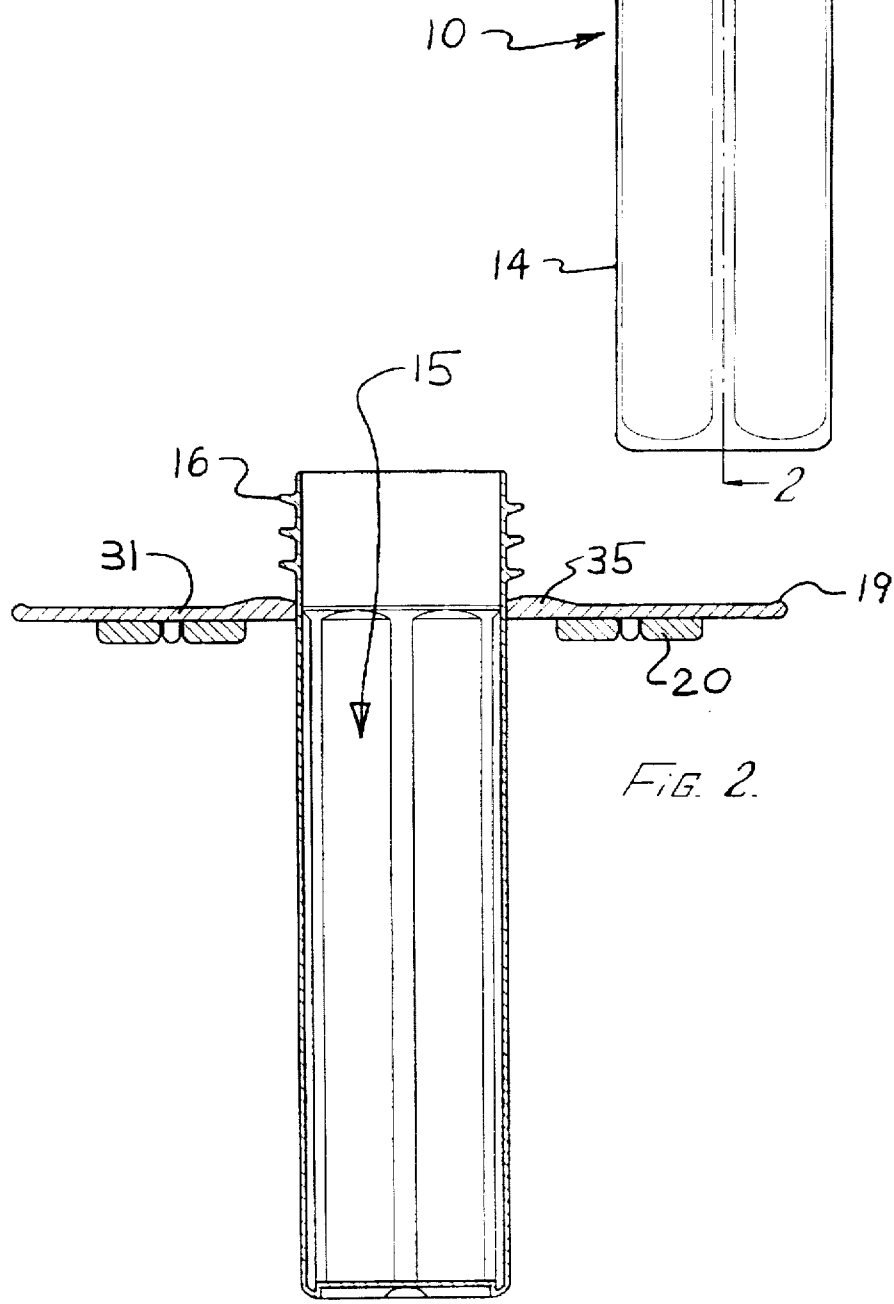

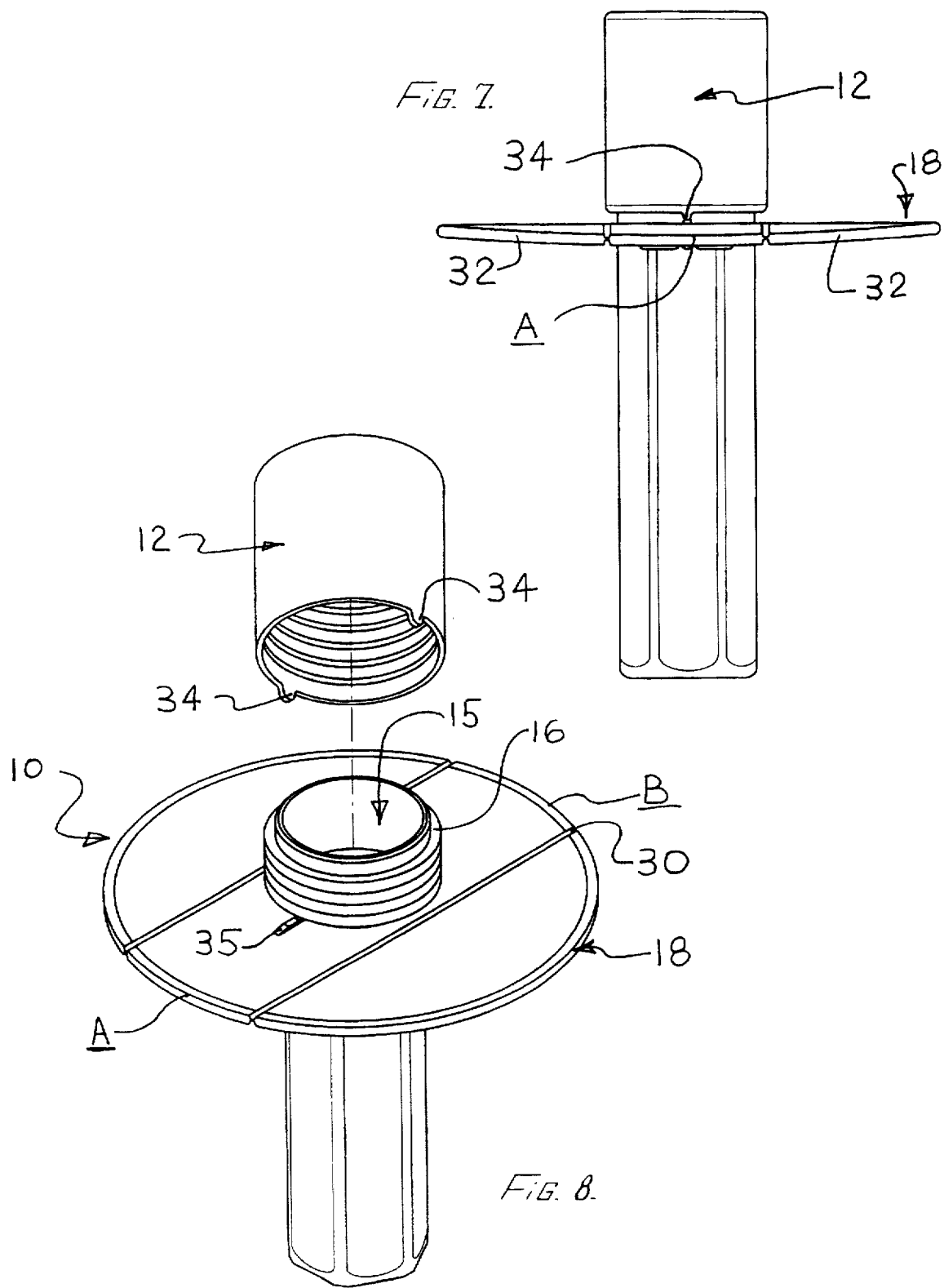

SURGICAL LIGHT HANDLE COVER

This is a continuation of application Ser. No. 08/491,394, filed on Jun. 19, 1995, now abandoned.

BACKGROUND AND SUMMARY OF THE INVENTION

The present invention relates to an improved disposable light handle cover for movable overhead surgical light fixtures found in hospital operating rooms. Surgical lights typically consist of a luminaire with one or more electric lamps housed therein, and supported by a balanced suspension which permits vertical and angular movement of the light fixture. Medical personnel may adjust the position of the light fixture during surgical procedures by grasping a handle which projects from the face of the fixture.

In order to maintain sterility in the surgical environment, the handle is removably attached to the light fixture, typically by screw threads era surgical procedure, the handle is removed and either sterilized or simply disposed of, and a new sterile handle attached for the next operation. A threaded socket is provided in typical surgical light fixtures in order to accommodate various handles.

The present invention relates to a modified and improved version of the light handle described in U.S. Pat. No. 4,974,288 to Reasner, the specification of which is incorporated herein by reference. Reasner teaches a disposable plastic light handle which includes a threaded portion which can removably engage the threaded socket of a surgical light fixture, a hollow, slightly knurled handle portion, and a protective shield connected to the handle portion. Two grooves integrally formed on the shield act as living hinges which permit outboard sections of the shield to be folded down against the handle.

The general object of the present invention is to provide a disposable surgical light handle which represents an improvement over the handle described in the Reasner patent. In particular, a light handle cover according to the present invention advantageously provides greater infection control in the sterile field. In addition, the handle of the present invention is intended to be more easily and inexpensively packaged for shipping and storage.

The removable handle of the present invention preferably includes a generally tubular handle, a circular shield, and a threaded portion. The circular shield includes two living hinges which permits the outboard sections of the shield to be folded down against the handle for storage. A plurality of tabs are advantageously disposed on the lower face of the shield, and a matching indentation formed on the lower end of the handle, to enable two handles to be frictionally engaged together by engaging the tabs of one handle with the indentations of the other. The handle is attached to a light fixture via an adapter which includes at least one projecting portion. The projecting portion presses against and deforms the circular shield and prevents movement of the living hinges, thereby causing the folding sections of the circular shield to be held rigidly in place while the handle is attached to the light fixture.

BRIEF DESCRIPTION OF THE DRAWING FIGURES

FIG. 1 is a side elevation view of the handle of the present invention;

FIG. 2 is a section view of the handle from the same angle as FIG. 1;

FIG. 7 is a side elevation view of the handle engaged with an adapter; and

FIG. 8 is a perspective view of an adapter about to be engaged to the handle.

DETAILED DESCRIPTION OF THE PREFERRED EMBODIMENT

Figure 3:
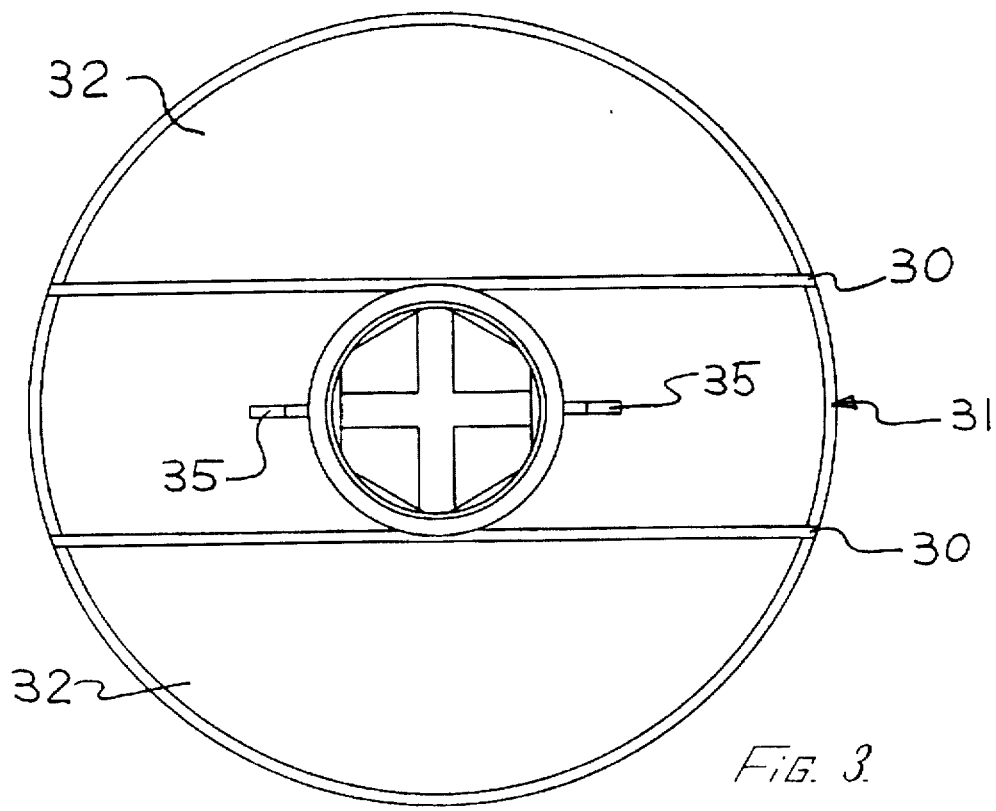
FIG. 3 is a top view of the handle.

As shown in FIG. 1, the present light handle 10 includes a hollow handle portion 14, a threaded portion 16, and a circular protective shield 18. The handle portion 14 may be circular in cross-section, or it may be hexagonal, as illustrated in FIGS. 1–8, in order to provide for greater leverage for grasping and turning. The handle may also be formed of any other generally polygonal shape. In addition, the surface of the handle may be knurled in order to further facilitate a positive grip. The handle 14 has a hollow interior 15 but is sufficiently strong to enable a surgeon or attendant to grab the handle and adjust a surgical light fixture (not shown) to which it is attached.

Figure 4:
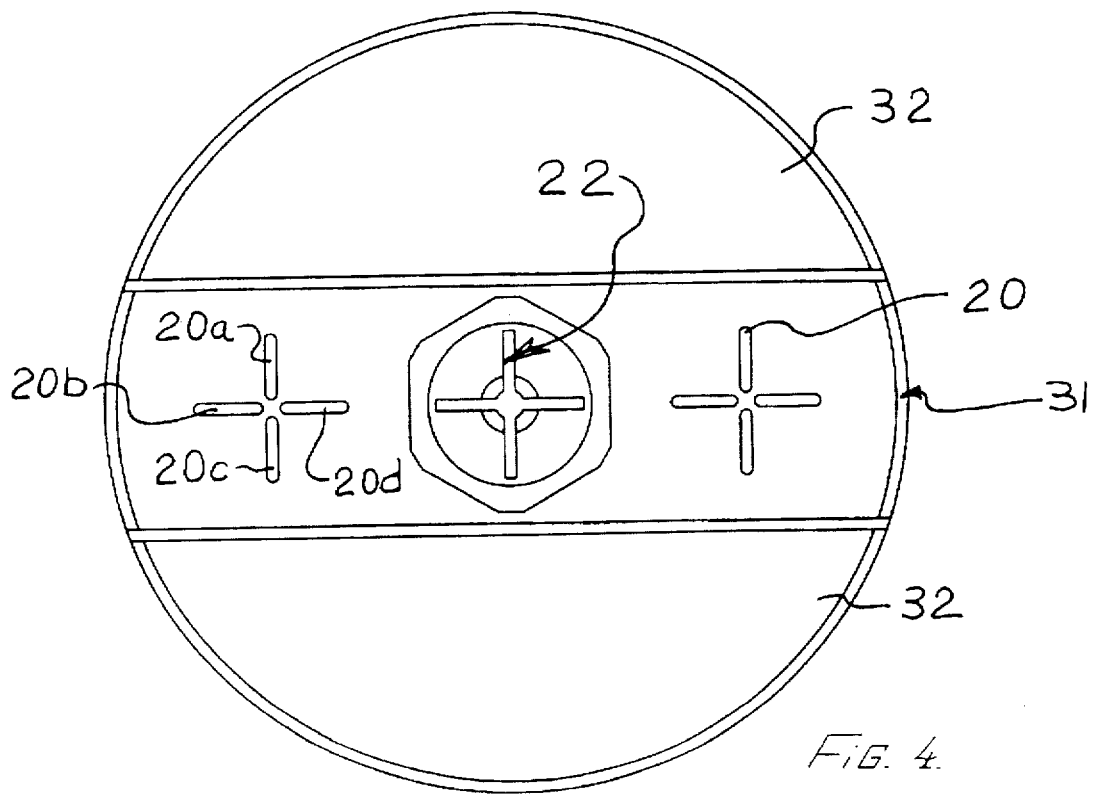
FIG. 4 is a bottom view of the handle.
Figure 5:
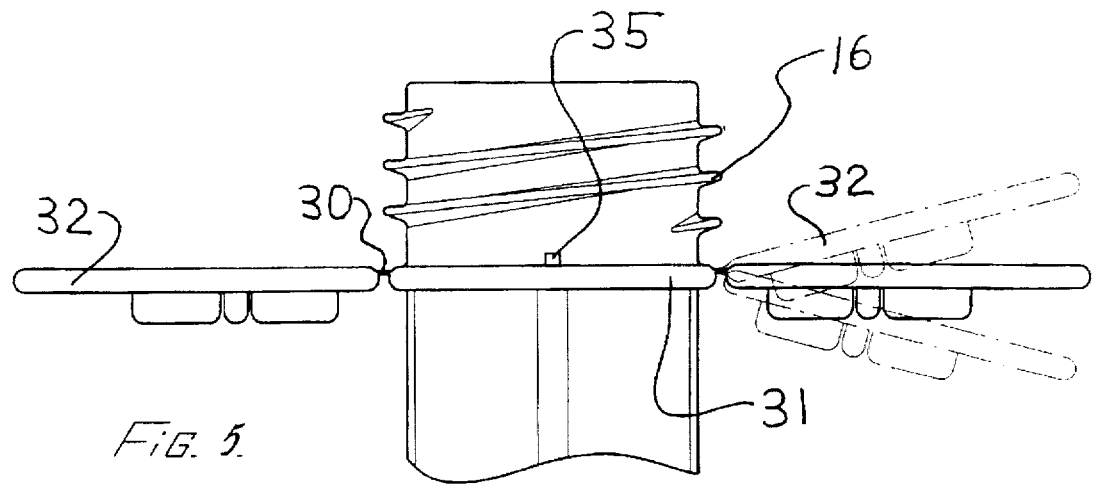
FIG. 5 is a partial side elevation view of the upper portion and shield of the handle.

The protective shield 18 is a relatively thin, flat disc surrounded by a small bead 19 of generally circular cross-section with a diameter slightly greater than the thickness of the shield 18. Preferably, the shield 18 is integrally molded with or connected to the handle 14. As shown in FIGS. 3 and 4, a pair of parallel hinge grooves 30 are formed in the lower face of the shield 18 and spaced relatively close to the threads of the handle 14. The grooves 30 divide the shield into a rigid central section 31 and a pair of outboard sections 32 of segmental shape pivotably connected to the central section. The grooves 30 are adapted to flex repeatedly without failure and allow the outboard sections 32 to be folded down against the handle 14, as shown in FIG. 5.

Four projecting tabs 20a, 20b, 20c, and 20d, are integrally molded into the bottom face of the central section 31 of the shield 18 and are arranged in the shape of a cross. The projecting tabs 20a, 20b, 20c, and 20d, collectively tabs 20, are shown in cross-section in FIGS. 1 and 2, and in the bottom view of FIG. 4.

FIG. 4 also shows a similar cross-shaped indentation 22 integrally molded into the bottom of the handle 14. The dimensions of the cross-shaped indentation 22 are approximately equal to the corresponding dimensions of the cross-shaped projecting tabs 20.

Although the projecting tabs 20 and indentation 22 are shown here in the shape of a cross, they may also be formed in various other arrangements or patterns.

Figure 6:
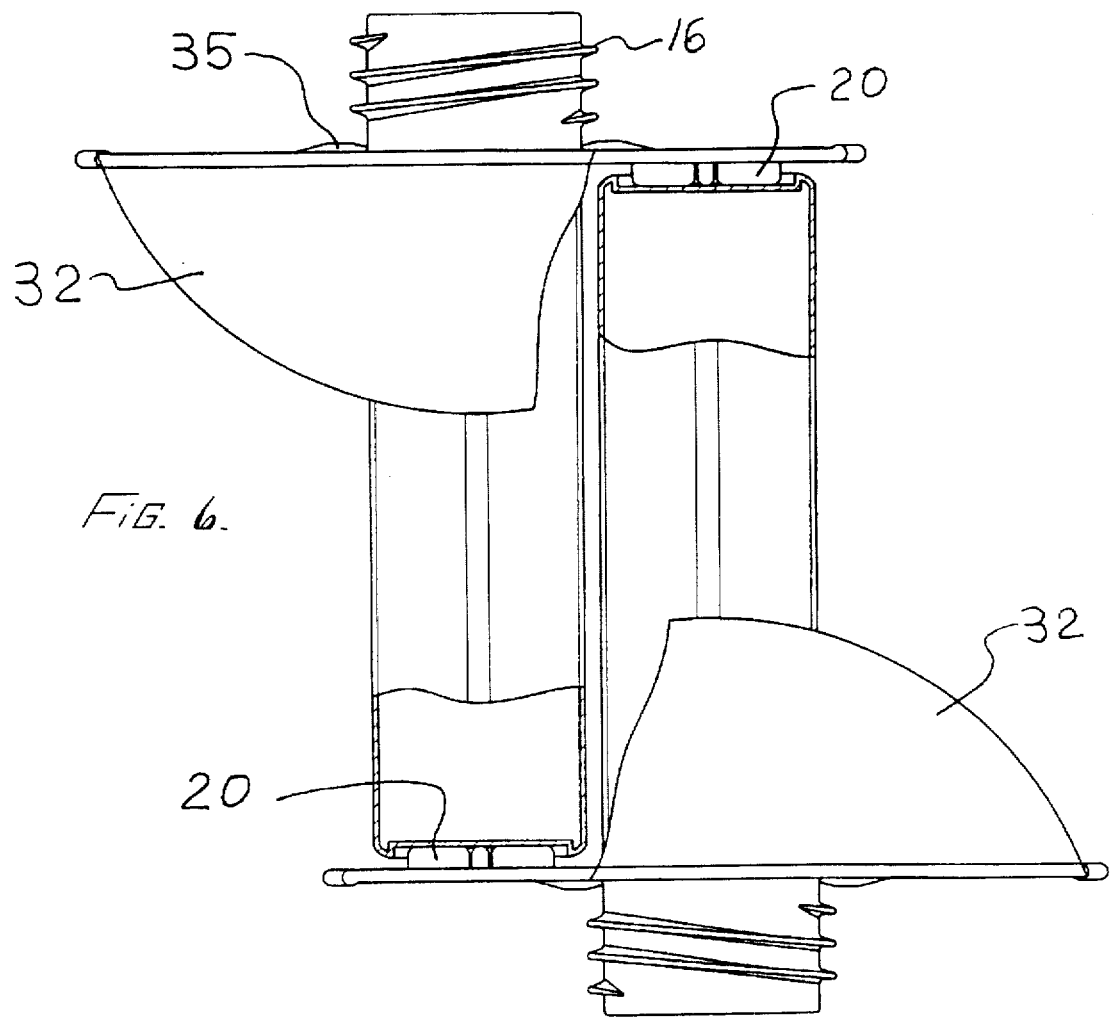
FIG. 6 is a side elevation view of two handles engaged together for packaging and storage.

Referring now to FIG. 6, the cross-shaped projecting tabs 20 and cross-shaped indentation 22 are adapted to enable the projecting tabs 20 of one handle to be engaged by frictional snap-fit into the indentation 22 of another (optionally identical) handle, so that two handles can be joined together for packaging and storage. In this arrangement, two handles are mutually aligned so that one of the projecting tabs 20 of each handle engages the indentation 20 of the other handle, and the outboard portions 32 of both are folded down against the handle portions 14 along the living hinges 30. Two handles can thus be arranged in a tight, space-saving configuration which expedites packing and shipping of the handles. The conventional paper band or binding used to join the handles is also eliminated, reducing hospital waste.

As shown in FIGS. 7 and 8, an adapter 12 comprises a hollow cylindrical body having screw threads in its interior adapted to engage the screw-threaded portion 16 of the handle 10. The upper portion of the adapter may also have screw threads (not shown) which allow the adapter to be engaged onto a conventional surgical lighting fixture.

The lower end of the adapter 12 also includes two ramps or projections 34 which project slightly beyond the lower flat end of the adapter. The number of screw threads, and the angular position of the start of the threads on the threaded portion and in the adapter are selected so that when the handle 10 is fully screwed onto the adapter 12, the projections 34 contact and exert a slight downward force against the central section 31 of the shield 18, as shown in FIG. 7. The projections 34 may be integrally formed contours of the adapter. Preferably, the threads on the threaded section and on the adapter 12 are arranged so that when the projection bottoms out on the central section, the projections are aligned generally parallel to the hinges. As shown in FIGS. 5 and 6, the threads are coarse, so that the adapter can be fully threaded on with 2–3 turns. Raised lands 35 may optionally be provided on the central section 31 as shown in FIGS. 3 and 8.

In operation, the screw threaded portion 16 of the handle 10 is inserted into and engaged with the interior of the adapter 12, and the adapter 12 is then engaged with a conventional surgical lighting fixture. The downward force exerted by the projections 34 against the central section 31 of the shield 18 causes the shield to bend or deform slightly, as shown in FIG. 7, so that the edges of the shield labelled A and B in FIG. 8 are pushed slightly downward relative to the center of the shield 18. The bending of the central section 31 of the shield 18 causes the entire disc to bend or bow slightly relative to the center of the disc. This bending action causes the hinge grooves 30 to become deformed as well, preventing them from flexing in their usual hinging action, which in turn causes the outboard portions 32 of the shield 18 to be held rigidly in place in the position shown in FIG. 7. Thus, when the handle 10 is properly engaged into the adapter 12 and attached to a surgical light fixture, the grooves 30 are locked against pivoting movement and the outboard sections 32 of the shield 18 are prevented from sagging against the handle portion 14. The outboard sections 32 therefore cannot interfere with a surgeon or nurse attempting to grasp and manipulate the light fixture. By preventing the hinges from flexing, the circular shield 18 is held rigidly in a relatively planar position while the handle 10 is attached to a light fixture.

The optional raised lands 35 act as stops, by inhibiting further turning of the adapter, when the projections are properly positioned onto central shield section. Instead of the projections on the adapter, the raised lands 35 can equivalently be made higher and wider, so that the same plate deforming and hinge locking action is achieved, with a flat bottom adapter pushing on raised projections on the central shield section.

The present invention thus provides an advantageous light handle which can be easily packaged and stored without the need for a paper band or other mechanism to hold two light handles together. The outboard sections 32 of the shield 18 can be folded down during packaging and storage, and two handles can be easily engaged together via the cross-shaped projections 20 and indentation 22. When the handles are attached to a surgical light fixture for use, the outboard sections are securely held in place and are prevented from folding down against the handle portion 14, by the deflection of the shield 18 caused by the projecting portions 34 of the adapter. When the surgical procedure is finished, the handle 10 can be removed from the light fixture and either sterilized for reuse or disposed of.

Thus, a novel lighting fixture handle has been shown and described. Many modifications may of course be made without departing from the spirit and scope of the invention.

I claim:

1. A handle set for a surgical lighting fixture, comprising:
   a first handle and a second handle, each comprising:
      a handle portion having a closed lower end;
      a central shield portion attached to the handle portion and having an upper and lower face;
      a pair of outboard shield sections attached to the central shield section by hinge joints, so that the outboard shield sections may be folded against said handle portion;
      an indentation in the lower end of the handle; and
      a plurality of projecting tabs disposed on the lower face of the shield;
   wherein the projecting tabs of the first handle are adapted to frictionally engage the indentation of the second handle, and the projecting tabs of the second handle are adapted to simultaneously engage the indentation of the first handle so as to removably secure the first and second handles together.

2. The removable handles according to claim 1, wherein the projecting portions are formed in the shape of a cross and said indentations are correspondingly formed in the shape of a cross.

3. A handle for a surgical lighting fixture comprising:
   a handle portion having a lower end;
   a shield attached to the handle portion;
   an indentation in the lower end of the handle; and
   a projecting tab on the shield.

4. The handle of claim 3 further comprising a pair of outboard shield sections attached to the shield by hinge joints.

5. The handle of claim 3 wherein the lower end is closed off.

6. The handle of claim 3 further comprising a plurality of projecting tabs.

7. The handle of claim 6 wherein the tabs are formed in the shape of a cross.

8. The handle of claim 3 wherein tab and the indentation have approximately equal dimensions.

9. A handle set comprising:
   a first handle and a second handle, each comprising:
      a handle portion having a lower end;
      a shield attached to the handle portion, the shield having an upper face and a lower face;
      an indentation in the lower end of the handle; and
      a projecting tab on the lower face of the shield;
   wherein the projecting tab on the first handle is adapted to frictionally engage the indentation of the second handle to secure the first and second handles together.

* * * * *